United States Patent [19]

Harrison

[11] 4,069,310
[45] Jan. 17, 1978

[54] METHOD FOR THE MANUFACTURE OF CLEAR DENTIFRICES

[75] Inventor: Michael Harrison, Ravenshead, England

[73] Assignee: Colgate Palmolive Company, New York, N.Y.

[21] Appl. No.: 640,123

[22] Filed: Dec. 12, 1975

Related U.S. Application Data

[60] Continuation-in-part of Ser. No. 403,985, Oct. 5, 1973, abandoned, which is a division of Ser. No. 197,499, Nov. 10, 1971, abandoned.

[30] Foreign Application Priority Data

Nov. 27, 1970 United Kingdom ............... 56575/70

[51] Int. Cl.$^2$ .............................................. A61K 7/16
[52] U.S. Cl. ...................................................... 424/49
[58] Field of Search .................................. 424/49–58; 252/316, 317

[56] References Cited

U.S. PATENT DOCUMENTS

| | | | |
|---|---|---|---|
| 3,378,445 | 4/1968 | Muhler | 424/49 |
| 3,506,757 | 4/1970 | Salzmann | 424/52 |
| 3,608,067 | 9/1971 | Irani | 424/52 |
| 3,642,979 | 2/1972 | Irani | 424/52 |
| 3,711,604 | 1/1973 | Colodney et al. | 424/52 |
| 3,728,446 | 4/1973 | Roberts et al. | 424/49 |
| 3,767,791 | 10/1973 | Cordon et al. | 424/49 |
| 3,840,657 | 10/1974 | Norfleet | 424/49 |
| 3,906,090 | 9/1975 | Colodney | 424/52 |
| 3,911,102 | 10/1975 | Harrison | 424/49 |
| 3,911,104 | 10/1975 | Harrison | 424/52 |
| 3,928,559 | 12/1975 | Patino et al. | 424/49 |
| 3,944,661 | 3/1976 | Coldney et al. | 424/49 |
| 3,946,108 | 3/1976 | Tomlinson et al. | 424/49 |
| 4,020,154 | 4/1977 | Perla et al. | 424/49 |

OTHER PUBLICATIONS

Neumann, et al., J. Soc. Cosmetic Chemists, vol. 21, pp. 255–258, Apr. 1, 1970.
Watson, J. Soc. Cosmetic. Chemists, vol, 21, p. 469, June 24, 1970.

*Primary Examiner*—Shep K. Rose
*Attorney, Agent, or Firm*—Robert L. Stone; Murray M. Grill; Herbert S. Sylvester

[57] ABSTRACT

A method for manufacturing a visually clear dentifrice from a substantially water-insoluble polishing agent having a refractive index of about 1.44 to 1.48, such as a colloidal silica, an amorphous silicic anhydride or an amorphous complex aluminosilicate, a synthetic inorganic complex silicate clay gelling agent of the formula $$[Si_8Mg_{5.1}Li_{0.6}H_{7.6}O_{24}]^{0.6-}Na^+_{0.6},$$

and a vehicle which includes water, sorbitol and glycerine, which method requires initial mixing of the gelling agent with a sorbitol solution in water to produce a clear gel, followed by admixing glycerine with said clear gel. The described manufacturing method results in quicker production of clear gels of the present formulations than do corresponding methods in which the gelling agent is initially mixed with glycerine or glycerine-containing mixtures. Also, it has been found that the gels made by the present method are of improved quality, compared to those in which gelation is initially attempted in glycerine instead of in aqueous sorbitol solution.

6 Claims, No Drawings

METHOD FOR THE MANUFACTURE OF CLEAR DENTIFRICES

This application is a continuation-in-part of my U.S. patent application Ser. No. 403,985, filed Oct. 5, 1973, now abandoned which is a division of my U.S. patent application Ser. No. 197,499, filed Nov. 10, 1971, now abandoned.

This application relates to clear dentifrices and especially to an improved method for their manufacture. More particularly, it relates to such a method wherein by a certain manufacturing sequence the time needed for production of clear gel from an inorganic gelling agent is diminished substantially and the gel quality is improved.

Dentifrices normally include a polishing agent, a humectant, water and a gelling agent and often also contain a synthetic organic surface active agent, which is usually a detergent. Among the various polishing agents that had been utilized there may be mentioned calcium carbonate, tricalcium phosphate, insoluble alkali metal metaphosphates and fluorophosphates, silicates and silicas, including amorphous complex aluminosilicates, which may be sold under the trademark Aerosil ®, such as Aerosil D200, amorphous silicic anhydrides, sold under the trademark Syloid ®, such as Syloid 72 and Syloid 74 and under the trademark Santocel ®, such as Santocel 100, and colloidal silicas, such as the fumed silicas sold under the trademark Cab-O-Sil ®, e.g., Cab-O-Sil M-5. When such polishing agents are of a refractive index like that of the rest of the dentifrice composition, which is usually about the refractive index of the humectant component(s) thereof, clear dentifrices may be produced. It has been found that the synthetic inorganic clay of the formula

sold as Laponite ®, makes an excellent gelling agent for clear dentifrices. However, the preparation of gels from the Laponite type of synthetic clay is often difficult or time-consuming. It has been taught that such synthetic clay gels react poorly to strong mixing (supposedly yielding gels of poor strength and stability) and the literature suggests that "Laponite" gels could be made by mixing with glycerine or with an aqueous medium containing glycerine. Also, in the production of dentifrices from the synthetic inorganic clays described, with polishing agents such as those selected from the group consisting of colloidal silica, amorphous silicic anhydride and amorphous complex aluminosilicates, sorbitol, glycerine and water, preferably also with synthetic organic detergent present, e.g., sodium N-higher fatty acyl sarcoside, it has been noted that the time to produce a desired clear gel during the process of manufacturing the described dentifrices is excessive when dispersing of gelling agent is effected according to "normal" techniques. The present invention is of a method by which such dispersing times are significantly diminished by a readily made modification of the manufacturing method.

In accordance with the present invention, a method for the manufacture of a visually clear dentifrice comprising a synthetic inorganic complex silicate clay gelling agent of the formula

a dentally acceptable substantially water-insoluble polishing agent having a refractive index of about 1.44 to 1.48, water, sorbitol and glycerine, with the proportions of dentifrice components being about 1 to 5% of gelling agent, about 5 to 50% of polishing agent and about 20 to 93.99% of a mixture of water, sorbitol and glycerine, comprises mixing said gelling agent with water and sorbitol to produce a clear gel and admixing glycerine with the clear gel. After production of the clear gel, to which the glycerine is subsequently added, the various other dentifrice constituents are admixed, preferably with the polishing agent being first added thereto, followed by an aqueous solution of the detergent. However, it is within the invention to add various dentifrice components along with the glycerine after manufacture of the water-sorbitol-gelling agent clear gel and while it is preferred to have no other materials present when such gel is being made, various compatible dentifrice adjuvants may be present too, usually in minor quantities and proportions, e.g., less than 5% each, preferably less than 1% each, on a finished product basis.

The gelling agent useful in the process of this invention to produce a clear dentifrice is a synthetic inorganic clay similar in constitution to the mineral hectorite but substantially free of undesirable quartz and dolomite impurities which contaminate hectorite. Several grades of the synthetic clay are available under the trademark Laponite (Laponite is a registered trademark of Laponite Industries Limited). Grades of Laponite synthetic clay which correspond to the formula set forth above are substantially free of fluorine (which is present in other grades of Laponite synthetic clay) and are available as Laponite CP and Laponite SP. The CP grade is particularly described in an article appearing in the "Journal of the Society of Cosmetic Chemists," Volume 21, No. 7 (Apr. 1, 1970), by Barbara S. Neumann and K. G. Sansom. The SP grade has a refractive index of 1.54 and has the following composition corresponding to the formula set forth above:

|  | PARTS |
|---|---|
| MAJOR COMPONENTS | |
| $SiO_2$ | 60.40 |
| MgO | 26.00 |
| $Li_2O$ | 1.10 |
| $Na_2O$ | 3.00 |
| $H_2O$ (structural) | 6.90 |
| IMPURITIES | |
| $Fe_2O_3$ | 0.02 |
| CaO | 0.20 |
| $SO_3$ | 0.10 |
| $CO_2$ | 0.29 |

The CP grade of Laponite synthetic clay having this composition has added to it a small amount, e.g., 0.1 to 2%, of polyphosphate electrolyte, which permits it to gel more rapidly upon contact with the liquid component of the dentifrice vehicle.

In preparing dentifrices it is often preferred to delay early gelling of the components in order to be able to deaerate the gel more readily. For this reason, it is often preferred to use the SP grade of Laponite synthetic clay which contains the same components, in the same amounts, as the CP grade, but to which electrolyte has not been added. Thus, when the SP grade is used the dentifrice components may be more readily deaerated under vacuum prior to gelling. Also, in such cases gelling may be accomplished in the presence of electrolytes provided as impurities in the polishing agents or by other components which may be employed, such as sodium N-lauroyl sarcosinate anionic surface active agent and sodium saccharin sweetener.

The polishing agent utilized in the practice of the invention has a refractive index of about 1.44 to 1.48. A refractive index in this range is desirable since the gel vehicle has a similar refractive index, thereby permitting the formulation of visually clear dentifrice preparations.

Suitable dentally acceptable polishing agents include colloidal silica or amorphous silicic anhydride having an average particle size of about 1 to 65 microns and a surface area of at least about 200 square meters per gram, which can exceed 600 m.$^2$/g. Most preferably, the range of surface area is about 200 to 400 m.$^2$/g. Among such agents are amorphous silicic anhydrides sold under the trademark Syloid as Syloid 72 and Syloid 74 and under the trademark Santocel as Santocel 100. These materials are additionally characterized as having a bulk density of about 0.15 to 0.30 g./cm.$^3$ and have refractive indexes of about 1.45 to 1.48.

Other excellent polishing agents are synthetic amorphous complex alkali metal aluminosilicate salts, particularly alkali metal salts such as sodium salts and alkaline earth metal salts such as calcium salts, which have a refractive index of about 1.44 to 1.47, up to about 20% by weight of moisture and up to about 10% by weight of alkali metal oxide or alkaline earth metal oxide.

The polishing agent employed is present in a proportion of about 5 to 50% by weight of the dentifrice. Preferably when the polishing agent is an aluminosilicate salt or a mixture thereof about 10 to 30% by weight is employed.

The gel or liquid vehicle of the dentifrice forms a mass of a consistency which desirably can be extruded from a collapsible tube such as an aluminum tube or a lead tube. The vehicle contains liquids and solids. In general, the liquid portion comprises water and glycerine. Sorbitol is usually employed as a 70% aqueous solution but is considered herein as a solid. It is usually advantageous to use a mixture of both water and a humectant such as glycerine, sorbitol or the like. The total liquid content is generally about 20 to 75% by weight of the visually clear dentifrice and typically includes about 5 to 30% by weight of water and 0 to about 60% by weight of glycerine. When the 20 to 70% by weight of sorbitol normally used is also included with the water and glycerine such mix content in the product is 20 to 93.99 or 94%. Normally when glycerine is present at least 5% thereof will be employed. Preferably about 5 to 20% by weight of water, about 15 to 35% by weight of glycerine and about 25 to 50% by weight of sorbitol are present in the dentifrice.

Sorbitol is suitably employed as a 70% by weight aqueous solution, which has a refractive index of 1.45. Glycerine alone or admixed with the sorbitol solution does not substantially alter this desirable refractive index from that of the polishing agent, since glycerine has a refractive index of 1.47. Thus, an aqueous gel of sorbitol and a substantial proportion of glycerine is eminently satisfactory. In a highly preferred method for the manufacture of the dentifrice initial operations include admixing the synthetic inorganic clay gelling agent earlier described with an aqueous sorbitol solution before any further ingredients are mixed therewith and especially before addition of glycerol. A clear gel may be produced by admixing all the sorbitol and all the water of the dentifrice formulation but some water may be withheld when it is needed to dissolve or disperse other dentifrice components, such as detergent, color solution, sweetener. The clear gel made from gelling agent, sorbitol, usually also with glycerol, and water is preferably produced by high shear mixing and as little as 1 to 5 or 15 minutes or such mixing may be sufficient. Alternatively, but not preferably, the production of the clear gel may take place by conventional mixing of the gelling agent and aqueous sorbitol at an elevated temperature, e.g., 90° C., for about 15 minutes. After dispersal of the gelling agent in the aqueous sorbitol satisfactory gelation occurs when glycerol is added and the mix is allowed to stand at room temperature for twelve hours or more. The proportion of gelling agent employed in the making of the clear gels described, on a final dentifrice basis, is about 1 to 5% by weight and preferably is about 1 to 3% by weight.

Organic surface active agents may be used in the compositions of the present invention to achieve increased prophylactic action, to assist in obtaining thorough and complete dispersion of the instant compositions throughout the oral cavity and to render the compositions more cosmetically acceptable. When an anionic surface active material is desired, substantially saturated higher aliphatic acyl amides of lower aliphatic amonocarboxylic acid compounds, such as those having 12 to 16 carbons in the higher aliphatic acyl group, are preferred and the higher aliphatic acyl is most preferably a higher fatty acyl. Examples of the last mentioned amides are N-lauroyl sarcosine, N-myristoyl sarcosine and N-palmitoyl sarcosine and the sodium, potassium and ethanolamine salts thereof, which should be substantially free from soap or similar higher fatty acid material which tends to substantially reduce the effects or these compounds. The use of these sarcosine compounds in dentifrice compositions of the present invention is particularly advantageous since they inhibit acid formation in the oral cavity due to carbohydrate breakdown and thereby help to prevent dissolution of tooth enamel in the oral medium. Alternatively, however, one may also employ other synthetic anionic organic detergents, such as sodium lauryl sulfate, sodium coconut oil fatty acids monoglyceride sulfate, sodium polyethoxy higher fatty alcohol sulfates and corresponding water soluble alkali metal, lower alkanolamine and ammonium salts of these and other known anionic detergents.

Other particularly suitable surface active materials include nonionics, such as the condensates of sorbitan monostearate with approximately 60 moles of ethylene oxide, condensates of ethylene oxide with propylene oxide condensates of propylene glycol (Pluronics ®), and amphoteric agents, such as quaternized imidazole derivatives, which are available under the trademark Miranol ®, such as Miranol $C_2M$. Cationic surface active germicides and antibacterial compounds such as di-isobutylphenoxyethoxyethyl dimethyl benzyl ammonium chloride, benzyl dimethyl stearyl ammonium chloride, tertiary amines, having one fatty alkyl group (of from 12 to 18 carbon atoms) and two polyoxyethylene groups attached to the nitrogen (typically containing a total of from about 2 to 50 ethenoxy groups per molecule) and salts thereof with acids, and compounds of the structure

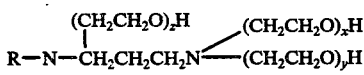

wherein R is a fatty alkyl group containing from about 12 to 18 carbon atoms, and x, y, and z total 3 or higher, e.g., 3 to 20, as well as salts thereof with mineral organic acids, e.g., HCl, may also be used. It is preferred to use from about 0.05 to 5% by weight of the foregoing surface-active materials in the instant oral preparations.

Any suitable flavoring or sweetening materials may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, sodium cyclamate, perillartine and saccharin. Suitably, flavor and sweetening agents may together comprise from about 0.01 to 5% of more of the composition of the instant invention and normally are from 0.002 to 4%, preferably 0.005 to 2.5% for each. The present invention dentifrices may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2.KF$), potassium fluorozirconate, sodium hexafluorostannate, stannous chlorofluoride and sodium monofluorophosphate. These materials, which dissociate or release fluorine-containing ions, suitably may be present in an effective but non-toxic amount, usually within the range of about 0.01 to 1% by weight of the water-soluble fluorine content thereof. Sodium fluoride, stannous fluoride and sodium monofluorophosphate are particularly preferred, as well as mixtures thereof.

Various other materials may be incorporated in the oral preparation of this invention. Examples thereof are coloring or whitening agents or dyestuffs, preservatives, silicones, chlorophyll compounds, ammoniated materials such as urea, diammoniumphosphate and mixtures thereof, and other constituents. The adjuvants are incorporated in the instant compositions in amounts which do not substantially adversely affect the properties and characteristics desired and are selected and used in proper amounts depending upon the particular type of preparation involved.

Antibacterial agents which may be employed in the oral preparations of the instant invention are usually present to the extent of 0.01 to 5%, preferably 0.05 to 1% of the dentifrice. Such agents are phenolic compounds, chlorinated materials, tin salts, quaternary ammonium compounds and suitable enzymes, e.g., cetyl trimethyl ammonium bromide.

Synthetic finely divided silicas such as those sold under the trademarks Cab-O-Sil M-5, Syloid 244, Syloid 266 and Aerosil D200 may be also employed in addition to the Laponite gelling agent in amounts of about 0.5 to 20%, e.g., 1 to 5% by weight, to promote thickening or gelling and to improve clarity of the dentifrice. Some such thickeners, such as the finely divided silicas, may also exert a polishing effect.

In the manufacturing of dentifrices it is convenient to remove entrained air from the product by deaeration under vacuum, typically at a late stage in the manufacture. In an aspect of the instant invention, it has been observed that in clear dentifrice gels of suitable viscosity the dispersed, immobile air bubbles may desirably enhance the appearance of the dentifrice and can therefore be permitted to remain therein. Furthermore, air can be at least partially removed and reintroduced as substantially globular or spheroidal bubbles of about 0.1 to 8 mm., preferably about 0.5 to 5 mm. in size (diameters), well distributed in the gel at an average of about one per cubic centimeter. Such air bubbles may be placed in the gel by stirring it while introducing air. Instead of air, bubbles of another gas, such as nitrogen or carbon dioxide, can be introduced in non-toxic quantity. In particular, carbon dioxide can provide an effervescent character to the dentifrice.

In the event it is desired to have a minimum amount of air in the dentifrice, or only to have to remove a minimum amount of air from the dentifrice of the instant invention, the Unimix apparatus described in *Process Engineering*, Sept. 11, 1970, pages 81–85, is particularly efficacious for this purpose. In this apparatus a mixing tool can be rotated in clockwise or counterclockwise manner and the action of the mixing tool is followed by the action of a scraper blade to ensure that the working surface of the apparatus is scraped clean. The positioning of the mixing tool and the scraper from the raised central column in the apparatus and the further presence of a hydraulically operated vacuum-tight lid permits but little air to enter the formulation during processing. Thus, the gelling agent, sorbitol and water can be efficiently blended in the Unimix apparatus. Then the glycerol can be separately blended with the clear gel polishing agent produced and additional components (except for post-added components, such as flavoring oil) may be admixed in the Unimix apparatus, and then the constituents to be post-added may be further admixed, preferably with all operations taking place under vacuum and with the various ingredients being deaerated before admixing. Gel and polishing agent pre-mixes can be made and can be separately deaerated and may be blended together under vacuum, for further deaeration or to maintain their degassed state. The Unimix or similar high shear apparatus can be used to blend the dentifrice components together at room temperature or at higher temperatures, e.g., 20° to 70° C.

If desired, visible particles of dyes, pearlescent flakes or particles of insoluble salts of antibacterial agents, as well as other particles, can be distributed in the dentifrice, The following examples illustrate but do not limit the invention. All amounts and proportions are by weight in the examples and in the specification and all temperatures are in ° C. unless otherwise mentioned.

EXAMPLE 1

32 Parts of sorbitol in a 70% sorbitol solids aqueous solution and two parts of Laponite SP synthetic clay are mixed under a vacuum of about 720 millimeters of mercury for about 10 to 15 minutes in a high speed, high shear Silverson mixer, equipped with a vacuum connection, which produces a clear gel. To the deaerated gel obtained there are added 25 parts of glycerine, followed by two parts of sodium N-lauroyl sarcosinate and 0.1 part of sodium saccharin. After the making of the initial aqueous sorbitol-Laponite gel the subsequent mixings are conducted in a Unimix mixer under the same vacuum and, although it is not usually considered to be essential, in a preferred embodiment of the invention the components or most of them are deaerated before mixing. Three parts of Aerosil D200 and 16 parts of sodium aluminosilicate complex of the type previously described, containing about 6% of moisture (measured by loss at 105° C.) and about 7% by weight of sodium oxide and having a refractive index of about 1.46, an average particle size (diameter) of about 35 microns and a sieved loose bulk density of 0.07 g./cc., are then vigorously mixed with the rest of the composition under vacuum in the Unimix mixer and mixing is continued for about ten minutes to produce a clear gel. The preceding mixing of the other components with the original aqueous sorbitol-Laponite gel takes about 15 minutes. Subsequently, one part of flavor, one part of aqueous color solution and 6.3 parts of water are admixed sequentially with the rest of the composition and a cosmetically satisfactory, visually clear and effective cleaning and polishing dentifrice results.

In modifications of this procedure, a Vibroreactor type of mixer of the Unimix mixer is employed for the initial production of the clear aqueous sorbitol-Laponite gel, preferably with the Unimix, if used, being adapted for high shear mixing. When using the Vibroreactor the gap setting is about 300 microns, the speed thereof is about 3,000 revolutions per minute and mixing is not under vacuum but immediately after passage through the Vibroreactor about ten minutes of mixing in the Unimix apparatus is effected to deaerate the product and to obtain a clear gel.

In addition to apparatus modifications, the dentifrice formula may be changed and when equivalent amounts of Syloid 72 and 79 or a mixture thereof is employed in replacement of all or part of the sodium aluminosilicate (when partial replacement is effected it is usually of ¼ to ¾ of the synthetic amorphous complex sodium aluminosilicate and when mixtures are employed they are usually of 1:3 to 3:1 ratios of the Syloids) and when the sodium N-lauroyl sarcosinate is replaced by sodium lauryl sulfate, sodium hydrogenated coconut oil fatty acids monoglyceride sulfate, sodium paraffin sulfonate, sodium alpha-olefin sulfonate, sodium higher fatty alcohol polyethoxy sulfate (all of known commercial types) or is partially replaced by a nonionic detergent such as Pluronic F-68 (block copolymer of ethylene oxide and propylene oxide) a similarly effective gel is made and a good dentifrice results. Also, when a mixture of Pluronic F-68 or similar solid or normally waxy (liquids may be used, too) nonionic surface active agent is utilized with a cationic detergent, normally with 1 to 5 parts of the nonionic to one part of cationic (the cationic detergent employed may be such as benzyldimethylstearyl ammonium chloride) good gels result, which is also the case when instead of the cationic compound there is employed an amphoteric surface active agent such as a quaternized imidazole derivative, e.g., Miranol $C_2M$.

In some variations of the formula there is present an antibacterial agent useful in dentifrices, such as a halogenated salicylanilide or a phenolic material or the surface active agent employed, such as a quaternary compound or sodium lauryl sulfate, is utilized for its antibacterial action. Of course, the various flavors, colors and other "incidental" adjuvants are also varied without changing the essential nature of the product.

In the various modifications of the formulation described above when the initial gelation of the Laponite is with an aqueous sorbitol solution and glycerine is added later good gels are obtained. Even when approximately half the sorbitol is used for the initial gelation and a mixture of glycerine and sorbitol is subsequently added, after the first production of the clear gel, good product results. However, in the described examples, when initially it is attempted to product the gel by admixing glycerine and Laponite, gelation time needed is longer and the gel obtained is not as strong. This is also the case when some glycerine is present with the aqueous sorbitol solution when the gel is initially made. Also to be kept in mind is the desirability of having some ionic materials or electrolyte present in the dentifrice composition to promote gelation of the Laponite in the dentifrice. Thus, in the above formulas approximately 0.1 to 1% of electrolyte is present as impurities in the polishing agent, detergent solution and sweetener and the various components, such as the detergent and the sweetener, can also exert "electrolyte effects" and assist gelation. When Laponite SP is replaced by Laponite CP it is not necessary for the electrolyte to be added but initial deaeration is not as readily achieved. When Laponite is replaced by sodium CMC or other organic gum the product made is less satisfactory.

EXAMPLE 2

The procedure of Example 1 is followed with the exception that instead of Laponite SP, Laponite CP synthetic clay is employed and during mixing in the high shear mixer (under air, not vacuum) bubbles of gas are intentionally left in the visually clear aqueous Laponite CP - sorbitol preliminary gel that has been produced. The various other components are then admixed [four parts of Syloid 244 are used instead of the three parts of Aerosil D200 and 15 parts of the sodium aluminosilicate complex (as in Example 1) are employed instead of the 16 parts used in Example 1], with the admixing being initially of the glycerine, surface active agent, sodium saccharin and antibaterial agent, when present, under 740 millimeters of mercury vacuum in a Unimix apparatus and with the mix of Syloid 244 and sodium aluminosilicate complex being admixed therewith in that apparatus, and the aerated mixture of sorbitol and Laponite CP synthetic clay being admixed with the other components (not under vacuum). A cosmetically desirable visually clear gel is obtained containing esthetically attractive bubbles.

In the other variations of formulas of Example 1 a bubbled dentifrice is also obtained by the method of this Example. Normally the bubbles are of air and of a diameter of about 1 to 3 millimeters, with an average of about one bubble per cubic centimeter, although higher concentrations, e.g., 2 to 10 or 20 bubbles/cc., may also be produced.

EXAMPLE 3

An aqueous solution of sorbitol containing 320 parts of sorbitol and 137 parts of water has mixed with it 30 parts of water, 1.5 parts of a 1% aqueous solution of F.D. & C. Blue No. 1 and 20 parts of Laponite CP in an in-line shear Vibroreactor (a Silverson high shear mixer may also be employed) at room temperature under the high shear conditions previously described. Mixing takes place over a period of about 10 minutes after the initial high shear dispersing of the Laponite and is under about 740 mm. Hg. vacuum. After using the Vibroreactor for about such a ten minute period another 10 minutes of mixing under vacuum in a Unimix type of mixer is desirable to obtain a clear Laponite gel and when the Silverson mixer is employed about 5 minutes of mixing therein, followed by 10 minutes of vacuum mixing in the Unimix apparatus is desirable for small batches, with larger batches, e.g., 2,000 lbs. taking up to 60 minutes, if heat is not employed. Mixing times may be lowered by using elevated temperature. Thus, without mixing with a high shear apparatus, at room temperature it takes about 16 hours to make an acceptable gel whereas by elevating the temperature to 40° C. this time may be cut to 1 hour and at 90° C. is about 15 minutes. Proportional reductions in mixing times are possible using the high shear mixers at elevated temperatures. When using elevated temperatures it is normally desirable to replace any water which may be lost due to evaporation. In such non-high shear mixing deaeration is also effected in a vacuum mixer, such as the Unimix apparatus.

Following the making of the deaerated aqueous sorbitol-Laponite gel the formula weight of glycerine, 250 parts, is mixed with the gel and the product resulting may be employed as a gel pre-mix for making any of a variety of dentifrices. Preferably the other components of the dentifrice, in the proportions described in Examples 1 and 2, are subsequently admixed, following the techniques of such example. Good clear, firm dentifrice gels result.

On the other hand, when glycerine is used instead of sorbitol in the initial disperion of the Laponite an unsatisfactory gel results and even when 20%, 40% and 60% of the glycerine is employed with sorbitol in the initial gelation operation longer mixing times are required (15 minutes, 20 minutes and 27 minutes, respectively) and when all the glycerine is present in with the sorbitol in the initial gelation stage the mixing time is increased five-fold, from 12 minutes, with no glycerine, to 60 minutes. At the same time, the gels produced become softer as more glycerine is present in the initial operations.

The above procedures are carried out at room temperature (20° to 25° C.) but similar results are obtained at elevated temperature operations too. Also, such results are typical of the manufacture of Laponite-gelled dentifrices when sorbitol and glycerol are present therein, when the polishing agent, surface active agent and adjuvants are changed, as described in Examples 1 and 2, and when the dentifrice includes fluoride compounds, too, e.g., stannous fluoride, sodium fluophosphates, etc.

The above invention has been described with respect to various illustrative examples and embodiments thereof but is not to be considered as being limited to these because it is evident that one of skill in the art with the present disclosure before him will be able to utilize substitutes and equivalents without departing from the spirit of the invention.

What is claimed is:

1. A method for the manufacture of a visually clear, bubble-free dentifrice comprising a vacuum deareated synthetic inorganic complex silicate clay gelling agent of the formula

a dentally acceptable substantially water-insoluble polishing agent having a refractive index of about 1.44 to 1.48, water, sorbitol and glycerine, with the proportion of such dentifrice components being about 1 to 5% of such gelling agent, about 5 to 50% of such polishing agent, about 5 to 30% of water, about 20 to 75% of sorbitol and at least 5% of glycerine, with the total of water, sorbitol and glycerine being about 30 to 94%, which comprises high shear mixing said deaerated gelling agent, heated to about 90° C. for about 15 minutes, 40° C. for one hour or unheated at room temperature for 16 hours, with water and sorbitol to produce a clear gel and admixing glycerine with the clear gel to make a clear water-sorbitol-glycerine gel.

2. A method for the manufacture of a visually clear dentifrice comprising a synthetic inorganic complex silicate clay gelling agent of the formula

a dentally acceptable substantially water-insoluble polishing agent having a refractive index of about 1.44 to 1.48, water, sorbitol and glycerine, with the proportion of such dentifrice components being about 1 to 5% of such gelling agent, about 5 to 50% of such polishing agent, about 5 to 30% of water, about 20 to 75% of sorbitol and at least 5% of glycerine, with the total of water, sorbitol and glycerine being about 30 to 94%, which comprises mixing said gelling agent with water and sorbitol to produce a clear gel and admixing glycerine with the clear gel to make a clear water-sorbitol-glycerine gel.

3. A method according to claim 2 wherein the dentifrice composition commprises 1 to 3% of the gelling agent, 10 to 30% of the polishing agent, 5 to 20% of water, 25 to 50% of sorbitol, 15 to 35% of glycerine and 0.05 to 5% or organic surface active agent, the polishing agent is selected from the group consisting of colloidal silica, amorphous silicic anhydride and amorphous complex aluminosilicates, and mixtures thereof, and has a refractive index in the range of 1.44 to 1.48, and the gelling agent is mixed with an aqueous solution of sorbitol to produce the clear gel, after which glycerine is admixed with the clear gel and with the product resulting there are subsequently admixed the polishing agent and organic surface active agent.

4. A method according to claim 3 wherein the polishing agent is a mixture of amorphous silicic anhydride and synthetic amorphous complex sodium aluminosilicate, the gel comprising gelling agent, water, sorbitol and glycerine is subjected to vacuum to deaerate it and subsequently a deaerated mixture of the amorphous silicic anhydride and synthetic amorphous complex sodium aluminosilicate is vigorously mixed with the other dental gel components to produce a clear gel.

5. A method according to claim 3 wherein the clear gel of sorbitol, water and gelling agent is made by high shear mixing and the clear gel produced is deaerated by mixing thereof under vacuum.

6. A method according to claim 4 wherein the gelling agent is free of gelation-promoting electrolyte, the surface active agent is a sodium N-higher fatty acyl sarcoside, sodium saccharin is present as a sweetener and there is present in the sarcoside and saccharin sufficient electrolyte to promote gelation of the gelling agent.

* * * * *